United States Patent
Pham

(10) Patent No.: US 10,716,322 B1
(45) Date of Patent: Jul. 21, 2020

(54) ORAL/ENTERAL VEGETARIAN FOOD COMPOSITIONS AND METHOD OF MANUFACTURING THE SAME

(71) Applicant: Duat Tien Pham, Ho Chi Minh (VN)

(72) Inventor: Duat Tien Pham, Ho Chi Minh (VN)

(73) Assignee: ORGALIFE NUTRITION SCIENCE COMPANY LIMITED, Ho Chi Minh (VN)

( * ) Notice: Subject to any disclaimer, the term of this patent is extended or adjusted under 35 U.S.C. 154(b) by 0 days.

(21) Appl. No.: 16/842,725

(22) Filed: Apr. 7, 2020

Related U.S. Application Data

(63) Continuation-in-part of application No. 16/026,068, filed on Jul. 3, 2018.

(51) Int. Cl.
| | |
|---|---|
| *C12N 9/00* | (2006.01) |
| *A23L 33/00* | (2016.01) |
| *A23L 33/105* | (2016.01) |
| *A23L 33/175* | (2016.01) |
| *A23L 33/185* | (2016.01) |
| *A23L 33/155* | (2016.01) |
| *A23L 33/16* | (2016.01) |
| *A61J 15/00* | (2006.01) |
| *A23L 19/00* | (2016.01) |
| *A23L 3/00* | (2006.01) |
| *A23L 3/3571* | (2006.01) |
| *A23L 3/40* | (2006.01) |
| *A23J 3/16* | (2006.01) |
| *A23J 3/18* | (2006.01) |
| *A23L 31/00* | (2016.01) |

(52) U.S. Cl.
CPC .................. *A23L 33/40* (2016.08); *A23J 3/16* (2013.01); *A23J 3/18* (2013.01); *A23L 3/003* (2013.01); *A23L 3/3571* (2013.01); *A23L 3/40* (2013.01); *A23L 19/01* (2016.08); *A23L 31/00* (2016.08); *A23L 33/105* (2016.08); *A23L 33/155* (2016.08); *A23L 33/16* (2016.08); *A23L 33/175* (2016.08); *A23L 33/185* (2016.08); *A61J 15/0003* (2013.01)

(58) Field of Classification Search
CPC ....................................................... C12N 9/00
See application file for complete search history.

(56) References Cited

PUBLICATIONS

Google Patents translation of Capital Medical Beijing Friendship University, CN 107156821 A, published on Sep. 15, 2017.*
Google Patents translation of Sun et al., Chinese Academy of Sciences, CN 101703248 A, 2010.*

* cited by examiner

*Primary Examiner* — Rosanne Kosson

(57) ABSTRACT

Vegetarian oral and enteral foods and processes for manufacturing the same from either fresh ingredients or powder ingredients are disclosed comprising: a high-protein vegetable group having a first predetermined percentage (%) weight; a carbohydrate group having a second predetermined percentage (%) weight; a fiber group having a fourth predetermined percentage (%) weight; purified water having a sixth predetermined percentage (%) weight, enzyme having a fourth percentage (%) weight; and a supplement of vitamins and minerals having a fifth percentage (%) weight, all undergon an enzymatic hydrolysis to achieve a calorie density of 1 kcal/ml; a viscosity less than 100 cP; a peptide less than 10 kDa; a plurality of amino acids and vitamins.

20 Claims, 4 Drawing Sheets

ORAL/ENTERAL VEGETARIAN FOOD COMPOSITIONS AND METHOD OF MANUFACTURING THE SAME

CLAIM OF PRIORITY

This application is a continuation-in-part (CIP) application under 37 C.F.R. § 1.53(b)(2) and 35 U.S.C. § 121 of the previously filed application Ser. No. 16/027,266, entitled, "Oral/Enteral Nutritious Foods and Methods of Manufacturing the Same", by Duat Tien Pham; which, in turn, claims priority under 35 U.S.C. § 119 of an application No. 1-2018-02610 filed on Jun. 18, 2018 in the Socialist Republic of Vietnam.

FIELD OF THE INVENTION

The present invention relates generally to the field of food nutrition. More specifically, the present invention relates to vegetarian food composition which can be administered in forms of oral admission for patients, enteral tube feeding (ETF) nutrition for seriously ill patients, and oral food supplements for people who want to supplement their daily diets with complete vitamins quintessential for a healthy body.

BACKGROUND ART

Enteral tube-feeding (ETF) of foods are designed to provide nutrition for seriously ill patients who cannot feed themselves. Such seriously ill patients include patients who are suffered from strokes, comatose, brain injury, etc. The benefits of ETF nutrition in critically ill patients are well known that include maintenance of caloric intake, health, the functional and structural integrity of the gut, decreased infectious complications, shorter hospital stays, and lower mortality. Often, tube feeding patients experienced more days with elevated gastric residual volume (GRV), constipation, vomiting, diarrhea, reflux, aspiration, abdominal distention, or cramping.

Because of the conditions of the patients, enteral tube-feeding (EFT) foods are made in form of liquid so that they can provide sufficient caloric intake in order to maintain the patient's health and resistance to illnesses. Even though worldwide medical food market has provided food formulas served these purposes, the majority of the food formulas is a composition based on well-known chemical elements such as glucose, maltodextrin, fructose, premade carbohydrate, nitrite casemate, or calcium casemate, amino acid, protein, and other milk products. These pre-processed food ingredients are expensive and lack of natural nutrients contained in foods. Moreover, a few pre-processed composite food formulas have high absorption pressure that can cause a prolonged bout of diarrhea and dehydration. In addition, the consumption of dairy foods or products rich in lactose found in milk can cause people with lactose intolerance severe indigestion and diarrhea.

Before the conventional commercial tube-feeding foods described above are available in the world market, families, loved ones, nurses, and nutrition department in hospitals often prepared different sorts of pureed soups for seriously ill patients. These pureed soups are still used in hospitals in many parts of the world. However, these pureed soups have no standards for patients with the same illness because they are prepared by different hospitals, different families with different formulas and cooking styles. Furthermore, these pureed soups are not subject to stringent quality controls. Therefore, they have different nutrition qualities and a short spoilage time. Commercial food processing machines, blenders, juicers, etc. can grind food ingredients into fine morsels. However, without being subject to a hydrolysis processing, these foods suffer from problems such as low homogenization and high viscosity. As a consequence, these foods cannot pass through the feeding tubes, which chokes and lowers the digestion capability of the patients. These problems are especially severe in patients who are seriously weak, having malfunctioning digestive system, and lacking of digestive enzymes.

In many developing countries like Vietnam, tube-feeding foods manufactured from natural ingredients that meet medical and nutritional standards have not been developed. There are a few companies that manufacture tube-feeding foods for patients. However, the proteins contained in these foods are made from vegetables mixed with assortments of imported materials. Therefore, they are expensive and do not have any nutrition standards for the same type of patients suffering from the same illness.

In addition, normal and healthy people may also be at risk for nutritional gaps. This is due to culture, habits, and ways of life. For example, in some countries, people consume mainly rice. In other cultures, people eat a lot of red meat in sausages, steaks, etc. Busy people have the habits of eating fast foods. Vitamin D can be hard to get in daily diet because it is only produced by the human body after exposure to the sun. Vitamin B6 is necessary for mental health. Roughly 1 to 10 Americans have low vitamin B6 levels. Many healthy women take oral contraceptives which lowers their B6 levels. As a consequence, women are twice as likely to be beficient in B6 as men, and are also twice as likely to be treated for mental depression. The reality is that nutrient deficiencies are far more prevalent than ever: suboptimal levels of key nutrients not only increase the risk for disease but also can negatively impact the mood, focus, and energy. Adopting a vegetarian diet can be the perfect way to stay healthy and happy.

Nowaday more and more people have adopted vegetarian diet because vegetarian diet is a complete diet, which is associated with high consumption of fiber, vitamins C and E, folic acid, magnesium, unsaturated fat, and numerous phytochemicals. And this is why vegetarians have lower cholesterol, lower blood pressure and reduced risk of heart diseases. Vegetarian food is also easy for the body to digest, takes lesser time to cook, is healthy. These are some benefits of a vegetarian diet: (a) increase life span, (b) lower cholesterol, (c) less risk of stroke and obesity, (d) reduce risk of diabetes, (e) have healthy skin, (f) reduce depression, (g) improve metabolism, (h) reduce the risk of cataract development, (i) economical, and (j) high fiber content. Thus, a vegetarian diet is is vital not just for the healthy living, the very sick people, and good for the environment.

Therefore what is needed is oral and/or tube-feeding medical foods and process of manufacturing the same that achieve food tolerance, meet nutritional requirements, inexpensive, and avoid serious side effects such as abdominal distention, gastroesophageal reflux, diarrhea, etc.

What is needed is a supplemental nutrition that can provide sufficient and complete nutrients in the daily diets for normal and healthy people so that they can avoid diseases and illnesses caused by the lack of important vitamins important to the human body.

Furthermore what is needed is a vegetarian oral/ethereal food composition that can provide complete and sufficient nutrition to both sick and healthy people.

SUMMARY OF THE INVENTION

Accordingly, an object of the present invention is to provide oral and enteral food which comprises: a high-protein meat group having a first predetermined percentage (%) weight; a high-protein vegetable group having a second predetermined percentage (%) weight; a carbohydrate having a third predetermined percentage (%) weight; a fiber having a fourth predetermined percentage (%) weight; purified water having a fifth predetermined percentage (%) weight, enzyme having a sixth percentage (%) weight; and a supplement of vitamins and minerals having a seventh percentage (%) weight, all enzymatic hydrolyzed to achieve a calorie density of 1 kcal/ml, a viscosity less than 100 cP, and chain peptides less than 10 kDa, amino acids such as leucine, aspartic acid, alanine, tyrosine, threonine, valine, lysine, serine, isoleucine, histidine, glutamic acid, methionine, cysteine, proline, tryptophan, phenylalanine, glycine, and arginine. Minerals and vitamins group is selected from a group consisting of vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and an iodine Another object of the present invention is to provide a process for manufacturing a oral/tube-feeding vegetarian food composition from powder ingredients which comprises: preparing high-protein vegetable ingredients in form of powder having a first predetermined percentage (%) weight, which includes, but not limited to: Vietnamese gingsen (*Panax vietnamensis*), *Angelica sinensis* gingsen, *Curculigo orchioides*, *Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, *Lentinula edodes*, oyster mushroom (*Pleurotus eryngii*), or combinations thereof; preparing carbohydrate ingredients in form of powder having a second predetermined percentage (%) weight, which includes, but not limited to rice, corn, potatoes, wheat, barley, quinoa, sugar beats, sorghum, millet, oats, secale cereal, *Sorghum nigrum*, millet seeds, macadamia, walnuts, cashew nuts, black garlic, tomatoes, grape fruits, kumquat, apples, or any mixtures thereof; preparing fiber ingredients in form of powder having a third predetermined percentage (%) weight, which includes, but not limited to: carrots, red pumpkins, cashew nuts, walnuts, macadamia, *Matricaria chamomilla, Hypericum calycinum*, various vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, tumerics, or their combinations thereof; adding enzyme having a fourth percentage (%) weight; adding a supplement of vitamins and minerals having a fifth percentage (%) weight; and adding purified purified water having a sixth predetermined percentage (%) weight—all introduced through processes such as enzymatic hydrolysis, cooking and pulverizing, ultra-filtering, homogenizing, sterilizing until the tube-feeding food composition achieves 1 kcal/1 ml with a food tolerance, a viscosity less than 100 cP, and chain peptides less than 10 kDa, and amino acids such as leucine, aspartic acid, alanine, tyrosine, threonine, valine, lysine, serine, isoleucine, histidine, glutamic acid, methionine, cysteine, proline, tryptophan, phenylalanine, glycine, and arginine. Minerals and vitamins group comprise vitamin A, vitamin $D_3$, vitamin E, vitamin $B_1$, vitamin B2, vitamin B3, vitamin B6, vitamin B12, vitamin B5, vitamin C, biotin, folic acid, potassium, sodium, magnesium, calcium, iron, zinc, phosphate, and an iodine.

Yet another object of the present invention is to provide process for manufacturing an oral/tube-feeding food composition made from fresh ingredients which comprises: preparing fresh high-protein vegetable ingredients having a first predetermined percentage (%) weight, which includes, but not limited to: Vietnamese gingsen (*Panax vietnamensis*), *Angelica sinensis* gingsen, *Curculigo orchioides, Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, *Lentinula edodes*, oyster mushroom (*Pleurotus eryngii*), or combinations thereof; preparing fresh carbohydrate ingredients having a second predetermined percentage (%) weight, which includes, but not limited to rice, corn, potatoes, wheat, barley, quinoa, sugar beats, sorghum, millet, oats, secale cereal, *Sorghum nigrum*, millet seeds, macadamia, walnuts, cashew nuts, black garlic, tomatoes, grape fruits, kumquat, apples, or any mixtures thereof; preparing fresh fiber ingredients in form of powder having a third predetermined percentage (%) weight, which includes, but not limited to: carrots, red pumpkins, cashew nuts, walnuts, macadamia, *Matricaria chamomilla, Hypericum calycinum*, various vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, tumerics, or their combinations thereof; adding enzyme having a fourth percentage (%) weight; adding a supplement of vitamins and minerals having a fifth percentage (%) weight; and adding purified water having a sixth predetermined percentage (%) weight—all introduced through processes such as enzymatic hydrolysis, cooking and pulverizing, ultra-filtering, homogenizing, sterilizing until the tube-feeding food composition achieves 1 kcal/1 ml with a food tolerance, a viscosity less than 100 cP, and chain peptides less than 10 kDa, and amino acids such as leucine, aspartic acid, alanine, tyrosine, threonine, valine, lysine, serine, isoleucine, histidine, glutamic acid, methionine, cysteine, proline, tryptophan, phenylalanine, glycine, and arginine. Minerals and vitamins group comprise vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and an iodinene.

Another object of the present invention is to provide a process for manufacturing a vegetarian food product which comprises: preparing high-protein vegetable ingredients having a first predetermined percentage (%) weight, which includes, but not limited to: Vietnamese gingsen (*Panax*

*vietnamensis*), *Angelica sinensis* gingsen, *Curculigo orchioides, Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, *Lentinula edodes*, oyster mushroom (*Pleurotus eryngii*), or combinations thereof; preparing carbohydrate ingredients having a second predetermined percentage (%) weight, which includes, but not limited to rice, corn, potatoes, wheat, barley, quinoa, sugar beats, sorghum, millet, oats, secale cereal, *Sorghum nigrum*, millet seeds, macadamia, walnuts, cashew nuts, black garlic, tomatoes, grape fruits, kumquat, apples, or their combinations thereof; preparing fresh fiber ingredients in form of powder having a third predetermined percentage (%) weight, which includes, but not limited to: carrots, red pumpkins, cashew nuts, walnuts, macadamia, *Matricaria chamomilla, Hypericum calycinum*, various vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, tumerics, or their combinations thereof; adding enzyme having a fourth percentage (%) weight; adding a supplement of vitamins and minerals having a fifth percentage (%) weight; and adding purified water having a sixth predetermined percentage (%) weight—all introduced through processes such as enzymatic hydrolysis, cooking and pulverizing, ultra-filtering, homogenizing, sterilizing until the tube-feeding food composition achieves 1 kcal/1 ml with a food tolerance, a viscosity less than 100 cP, and chain peptides less than 10 kDa, and amino acids such as leucine, aspartic acid, alanine, tyrosine, threonine, valine, lysine, serine, isoleucine, histidine, glutamic acid, methionine, cysteine, proline, tryptophan, phenylalanine, glycine, and arginine. Minerals and vitamins group comprise vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and an iodine.

Another object of the present invention is to provide medically and nutritiously standardized foods that can be used for seriously ill patients, for rehabilitating patients, for the elderly, or for healthy people who need to have supplements and/or substitutes for their daily diets, suitable for vegetarians.

Another object of the present invention is to provide medically and nutritiously standardized foods that can be introduced to users by either oral and/or enteral admission methods.

These and other advantages of the present invention will no doubt become obvious to those of ordinary skill in the art after having read the following detailed description of the preferred embodiments, which are illustrated in the various drawing figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Figure 1:
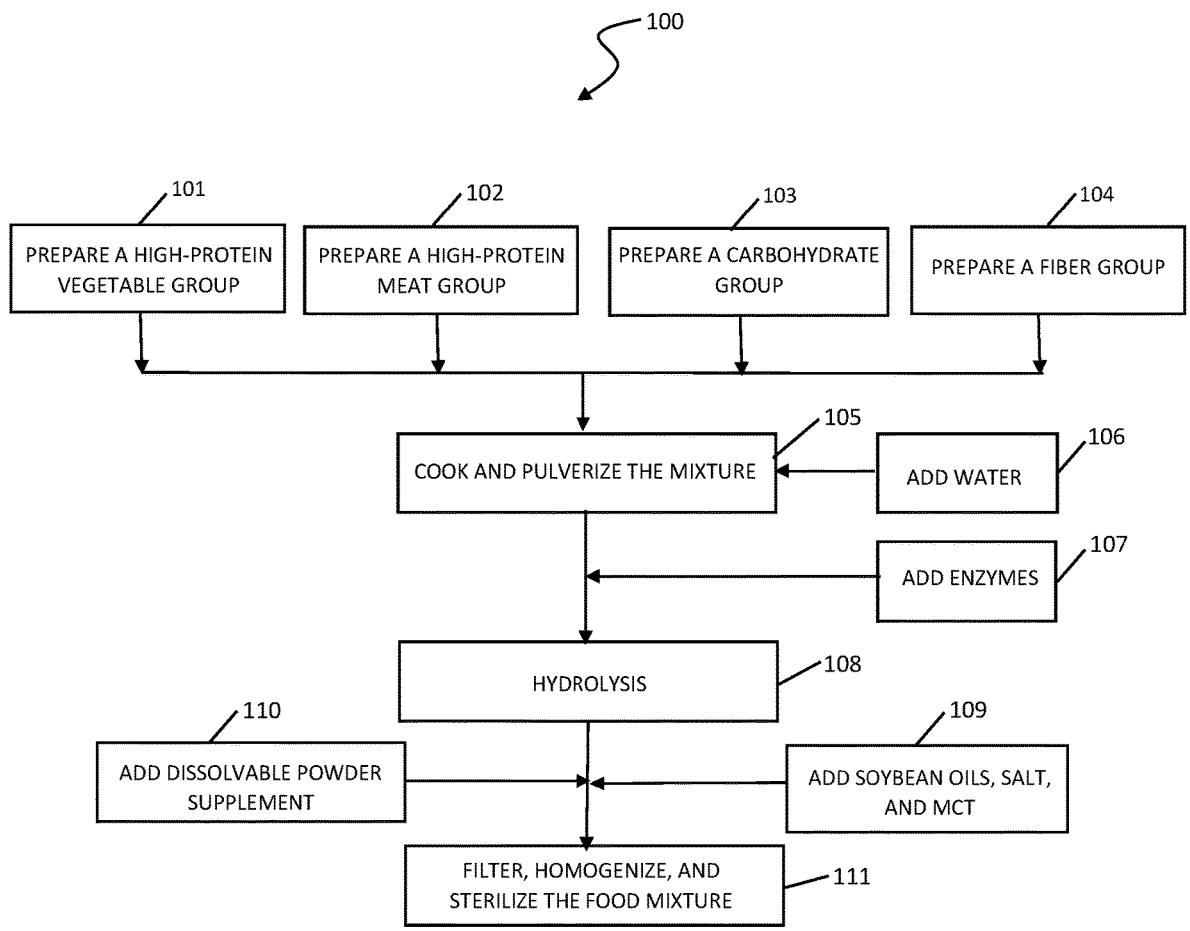
FIG. 1 is a flowchart illustrating an oral/ethereal nutritious foods made from a process in accordance with an embodiment of the present invention.

One embodiment of the invention is now described with reference to FIG. 1 illustrates an oral/enteral food product made from a process 100 in accordance with an exemplary embodiment of the present invention.

At step 101, a high-protein vegetable group having a first predetermined weight is prepared. In one exemplary embodiment of the present invention, the high-protein vegetable group is selected from *Panax vietnamensis, Angelica sinensis, Curculigo orchioides, Panax pseudoginseng*, South Korean gingsen, North Korean gingsen, Peruvian gingsen, *Ophiocordyceps sinensis, Abelmoschus sagittifolius*, American gingsen, *Polyscias fruticosa*, lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, lentinual edodes, oyster mushroom (*Pleurotus eryngii*), or any combinations thereof with 2-7% of total weight. In various embodiments, the high-protein vegetable group comprises other ingredients listed in Table 1 below.

TABLE 1

Examplary Vegetarian Food Composition Vegetable Ingredients (%)

| Ingredient | % |
|---|---|
| High protein vegetable group comprising Vietnamese gingsen (*Panax vietnamensis*), *Angelica sinensis* gingsen, *Curculigo orchioides*, *Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, glycine, green bean, potatoes, carrots, red pumpkins, macadamia, walnuts, almonds (amydala), *Momordica cochinchinensis*, green algae, curly kale, seaweeds, cauliflower, medicinal plants, medicinal herbs, *chenopodium quinoa*, avocado, spinach, cashew nuts, chia seeds, paddy straw mushrooms, *Lentinula edodes*, oyster mushroom (*pleurotus eryngii*) or the likes | 1-20 |
| Carbohydrate group comprising: rice, corn, potatoes, wheat, barley, quinoa, sugar beats, sorghum, millet, oats, secale cereal, sorghum nigrum, millet seeds, macadamia, walnuts, cashew nuts, black garlic, tomatoes, grape fruits, kumquat, apples, or the likes | 10-23 |
| Fiber group comprising carrots, red pumpkins, cashew nuts, walnuts, macadamia, *Matricaria chamomilla*, *Hypericum calycinum*, various vegetables, spinach, cauliflower, sweet potato, taro, different nuts such as black bean, red beans, peas, etc.; corn, artichokes flowers, chia seeds, lotus seeds, green tea, celery, catnip, *morinda officinalis*, black garlic, cabbage, strawberries, pears, banana, blackberries, apple, avocado, kiwi fruits, passion fruit, lemon, cucumbers, cantaloupes, ginkgo biloba, aloe vera, moringa, saffron, turmeric, or the likes. | 1-10 |
| Enzyme comprising the combinations of Celulase, Amylase, Lipase, and Protease; | 0.01-5 |
| Minerals and vitamins include: vitamin A, vitamin D3, vitamin E, vitamin B1, vitamin B2, vitamin B3, vitamin B6, vitamin B12, vitamin B5, vitamin C, biotin, folic acid, potassium (K), sodium (Na), Magnisium (Mg), Calicium (Ca), iron (Fe), Zinc (Zn), Phospor (P) and Iodine (I); | 0.01-3 |
| Purified water | 40-85 |

TABLE 2

Some Examplary Predetermined Guidelines for Selecting High-protein Vegetable Group:

| No. | Vegetable group | Standards |
|---|---|---|
| 1 | Soybean | Humidity 10-14%, protein content 33-39%, fatty content of 11-15%, whole grain, uniformly round, dry and clean, light yellow skin color, not soiled and infected and without odor, percentage of crack <5% total weight, percentage of rotten <2% impurities <3% of total weight |
| 2 | Rice | Components (in 100 g): humidity ≤14% (w/w), protein 8%, fat 1%, glucid 74-76%, impurities ≤0.1% (w/w), broken rice ≤5% (w/w), unusable ≤1.5%, yellow color ≤0.5%, unhusked rice ≤15 grain/kg, unripen ≤0.2%] |
| 3 | Potatoes | Humidity ~75% (w/w), protein >22%, fat <1%, glucid 18-21%, whole and unrotten tuber |
| 4 | Carrots | Humidity ~90% (w/w), protein 1.5-2%, fat 0.2-1%, glucid 8%, large tuber with bright yellow orange color, wholesome without rotten and crushed. |
| 5 | Pumpkins | Humidity ~92% w/w, Protein 0.3%, Fat 0.1%, Glucid 6.1% with Smooth, Slightly Pealed Skin, and Deep Yellow to Orange Color, Wholesome and Fresh. |
| 6 | Cereals and nuts | Maize, Wheat, Barley, Sorghum, Millet, Oats, Rye, Triticale, Fonio, Teff, macadamia, walnut, almond, etc. |
| 7 | Other vegetables, herbs, or medicinal plants | Vietnamese gingsen (*Panax vietnamensis*), *Angelica sinensis* gingsen, *Curculigo orchioides*, *Panax pseudoginseng*, South Koreran gingsen, North Korean gingsen, Peruvian gingsen, *Ophiocordyceps sinensis* (cartepillar fungus), *Abelmoschus sagittifolius*, American gingsen (Panax quinquefolius), *Polyscias fruticosa*, *Momordica cochinchinensis*, Lotus rhizome, green algae, curly kale, seaweeds, cauliflower, Fungus (*Lentinula edodes*, *Volvariella volvacea*, *Pleurotus eryngii*,...), *chenopodium quinoa*, avocado, spinach etc. |

After carefully selecting the above high-protein vegetable group according to the predetermined guidelines in Table 2, and other high-protein vegetable components listed in Table 1 above are carefully selected and gathered. Afterwards, they are cleaned and washed, minced into small pieces, and grinded into liquid. Soybeans are soaked in water, wash off their skins, and grinded into liquid. Finally, rice are soaked in water to wash off dirt and grinded into fine liquid.

Next, at step 102, a high-protein meat having a second predetermined percentage (%) weight is prepared. In one exemplary embodiment, the high-protein meat is selected from a group of (but not limited to) a fresh and lean pork, beef, other cattles such as sheep, lambs, goats, . . . seafood such as fishes, shrimps, etc.; chicken, ducks, other fowls, and edible insects such as rickets, larvae, grasshoppers, beetles, and flies, with 2-15% of total weight. Some examples of high-protein meat group are selected and prepared according to Table 3 below. In most implementations, the high-protein meats are cleaned, washed thoroughly, cut into small chunks, and ground with water into a composition of ground meat and water.

TABLE 3

Some Examples of Predetermined Guidelines for Selecting High-protein Meat Group

| | High-Protein Meat | Standards |
|---|---|---|
| 1 | Fresh and Lean Pork Meat Cut From Pork Shoulder | Fresh Pork Meat pH: 5-6.4 Humidity: 72.5-75.5% Protein 19-22% Fat 1.2-3%; Ash 0.5-1% (wet meat material); dry meat surface, clean, smooth without hairs and impurities, excellent meat. Meat is kept at 0° C. until used (max. 05 days). |
| 2 | Pork Powder | Made from fresh pork, typical color of dried pork powder, Size < 1 mm |

TABLE 3-continued

Some Examples of Predetermined
Guidelines for Selecting High-protein Meat Group

| | High-Protein Meat | Standards |
|---|---|---|
| | | Protein: 60-90% |
| | | Lipid: 6-10% |
| | | Moisture <= 8% |
| | | Bacterial and Metal Contents: Low |
| | | Impurities: Not Seen By Eyes |
| 3 | Other vertebrate Cattle | Cows, lambs, goats, ox |
| 4 | Fowl | Chickens, ducks, turkeys, etc. |
| 5 | Seafood | Fishes, shrimps, squids, octopi, etc. |
| 6 | Edible Insects | Crickets, larvae, grasshoppers, beetles, flies |

Continuing with step 102, in one exemplary embodiment, the determination of proteins, fat, and amino acid contents of the composition is performed by a Folch method. The amount of protein content in the meat group is carried out by a high performance liquid chromatography (HPLC) method. In the Folch method, the high-protein meat group is homogenized with chloroform/methanol to a final volume. After dispersion, the whole composition is agitated during 15-20 minutes in an orbital shaker at room temperature. Then, the homogenate is either filtrated or centrifuged to recover the liquid phase. The solvent is washed with water or NaCl solution. After vortexing some seconds, the food composition is centrifuged at low speed to separate the two phases. The removal of the upper phase by siphoning and kept it to analyze gangliosides or small organic polar molecules. After removing labelled molecules, rinse the interface one or two times with methanol/water without mixing the whole separation. After centrifugation and siphoning of the upper phase, the lower chloroform phase containing lipids is evaporated under vacuum in a rotary evaporator or under a nitrogen stream.

In some implementations of step 102, the high performance liquid chromatography (HPLC) method can be used. HPLC is a technique in analytical chemistry used to separate, identify, and quantify each component in the food composition. It relies on pumps to pass a pressurized liquid solvent containing the sample composition through a column filled with a solid adsorbent material. Each component in the sample interacts slightly differently with the adsorbent material, causing different flow rates for the different components and leading to the separation of the components as they flow out the column. HPLC can be described as a mass transfer process involving adsorption. HPLC relies on pumps to pass a pressurized liquid and the food composition through a column filled with adsorbent, leading to the separation of the sample components. The active component of the column, the adsorbent, is typically a granular material made of solid particles (e.g. silica, polymers, etc.), 2-50 μm in size. The components of the food composition are separated from each other due to their different degrees of interaction with the adsorbent particles. The pressurized liquid is typically a composition of solvents (e.g. water, acetonitrile and/or methanol) and is referred to as a "mobile phase". Its composition and temperature play a major role in the separation process by influencing the interactions taking place between sample components and adsorbent. These interactions are physical in nature, such as hydrophobic (dispersive), dipoledipole and ionic, most often a combination. Both Folch method and HPLC method are well known in the art and need not to be discussed in details here.

At step 103, the composition rich in carbohydrate is a third ingredient having a third predetermined percentage weight. In one implementation, carbohydrate is selected from rice, corn, potatoes, wheat, barley, quinoa, sugar beats, sorghum, millet, oats, secale cereal, *Sorghum nigrum*, millet seeds, macadamia, walnuts, cashew nuts, black garlic, tomatoes, grape fruits, kumquat, apples, or any mixtures thereof at 10%-18% by weight. They are selected according to the guidance of Table 2.

Next, at step 104, fiber having a fourth predetermined percentage (%) by weight is added. In some implementations, fiber is selected from carrots, red pumpkins, cashew nuts, walnuts, macadamia, *Matricaria chamomilla, Hypericum calycinum*, different vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, tumerics, or their combinations thereof at 1% to 5% by weight. The fiber is selected carefully according to the instructions of Table 2.

At step 105, high-protein vegetable group, high-protein meat, high-carbohydrate material, high-fiber material are mixed together into a composition. The composition is then cooked at 85 degrees Celsius for about 10-15 minutes to kill and/or suppress any micro-organism in the composition. At the same time, continuing with step 105, the composition is further pulverized into liquid. During the cooking process, the pH as well as viscosity of the food composition are constantly observed.

At step 106, purified water ($H_2O$) is added into the composition during step 105. Purified water having a predetermined weight of 65-90% is continually added into the composition.

Next, at step 107, catalytic enzymes having a third predetermined weight is added into the cooked and pulverized composition. In one exemplary implementation, enzymes is selected from a group of Alcalase$^R$ 2,4L, Flavourzyme® Protamex; Termamyl SC, Pectinex Ultra SP-L; Trypsin, Pepsin, a-chymotrypsin, Protease A "Amino" 2SD, Kleistase E5CC, v.v . . . a weight of 0.01% to 5% The standards of these enzymes are listed in table 3 below. In one exemplary embodiment, enzyme, soybean oil, and premix vitamins such as vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine having a weight of 0.01% to 3% of the total weight is used.

TABLE 4

Some Examples of Enzymes and Their Predetermined Selection Guidelines

| No. | Enzyme | Standards |
|---|---|---|
| 1 | Cellulase, Protease, Amylase, Lypase. | Activation: depending on types of enzymes, selected to guarantee successful product binding<br>Total bacterial count <100 CFU/g<br>Coliform bacteria: 4 CFU/g<br>Ecoli: Absent<br>Salmonella: Absent |

At step 108, the enzyme added composition of step 107 is undergone a hydrolysis process. The hydrolysis process is designed to create amino acids contained inside the ingredients described above, thus improving the nutrition value of the composition and the absorption capability of the user.

At step 109, soybean oils, salt, and medium chained triglycerides (MCT) is are allowed to dissolve into the composition. The aim of step 109 is to increase the food value and improve the tastes and feels of the composition.

At step 110 further supplementing powder fiber and dissolving them in the food composition to guarantee the sufficiency of fiber ingredients in the food products for the consumers.

Finally, at step 111, after the enzymatic hydrolysis process, the composition is undergone filtration, homogenization, and sterilization process prior to packaging. During filtration, the food composition is passed through to a Millipore membrane and an Amicon centrifugal filter unit, which guarantees the composition is in a liquid form. Millipore membrane and Amicon centrifugal filter unit are well known in the art and need not to be discussed here.

In an exemplary implementation of step 111, the homogenization is to enhance the stability of the fluid composition and to create the standardized tube-feeding foods for all seriously ill patients, as well as the demands of the consumers. After homogenization, the composition is passed through an ultra-heat treatment (UHT) apparatus at 135 to 142 degrees Celsius in a short time period from 4-10 seconds to kill all remainder microbes therein such that the ingredients are preserved in the food products.

The process 100 disclosed above achieved the following objectives:

Developed a formulation of raw materials for standard formula for tube-feeding or oral feeding foods achieves 1 kcal/1 ml with a food tolerance.

Selected suitable enzymes for food processing.

Optimized all factors that impact on the hydrolysis of raw materials to achieve a viscosity less than 100 cP tube-feeding foods and the appropriate proportion of short chain peptides less than 10 kDa, and amino acids such as leucine, aspartic acid, alanine, tyrosine, threonine, valine, lysine, serine, isoleucine, histidine, glutamic acid, methionine, cysteine, proline, tryptophan, phenylalanine, glycine, and arginine.

The nutritious food as described above in accordance with many aspects of the present invention includes: vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and an iodine.

The food processing is determined via oral and ethereal tube feeding methods from natural ingredients including fresh and powder materials.

Conducted an assessment of the digestibility in vitro.

Evaluated the protein digestibility of the product in animal models.

Implemented a controlled clinical trial in the patients in Hospital to evaluate the effectiveness (nutritional status) and tolerance of the tube feeding food produced from natural ingredients.

Taking together, these results showed very promising that we have enough capability and technology to develop a process in production of food supplement via oral and enteral administration methods from local natural ingredients. In addition, the effectiveness and tolerance of the product have been illustrated in clinical trial thus providing an opportunity to approach a cheaper but reliable product for not only critical patients who need nutrition supports while being hospitalized but outpatients who are discharged. The widely producing of this product should be considered and implemented worldwide.

Figure 2:
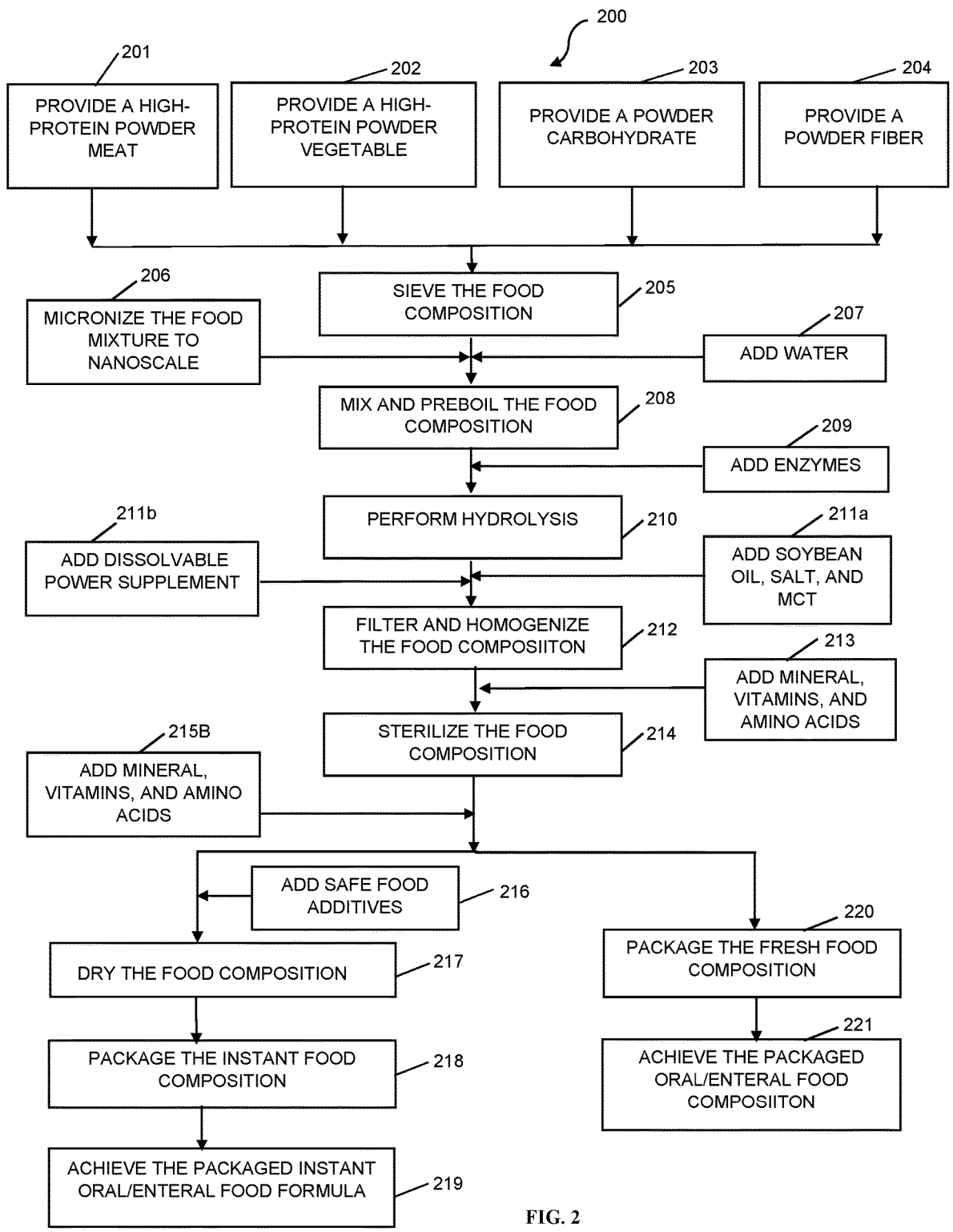
FIG. 2 is a flowchart illustrating a process of manufacturing an oral/enteral food of the present invention from powder ingredients.

Next referring to FIG. 2, a process 200 of manufacturing oral/enteral foods in forms of instant food formula or fresh nutritious food composition from various powder ingredients are illustrated. In some implementations, process 200 is used to produce either an instant oral or enteral food formula in a package. In some other implementations, process 200 is used to produce a nutritious oral or enteral food composition in a package. In this instant, the food is ready to be used by either oral or enteral administration.

At step 201, a high-protein meat powder having a first predetermined percentage (%) by weight is prepared. In one implementation, the meat powder is selected generally from farm animals, poultry, cattles, fowls such as chicken, pork, cow, goats, lambs, etc.; seafood including fish, shrimp; and other edible insects such as crickets, larvae, grasshoppers, beetles, flies, etc. at 2% to 8% by weight.

At step 202, a high-protein vegetable powder having a second predetermined percentage by weight is provided. In an implementation of step 202, the vegetable powder is selected from a group of Vietnamese gingsen (*Panax vietnamensis*), *Angelica sinensis* gingsen, *Curculigo orchioides*, *Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, *Lentinula edodes*, oyster mushroom (*Pleurotus eryngii*) at 1% to 5% by weight.

At step 203, a high-carbohydrate powder having a third predetermined percentage (%) by weight is provided. In one implementation, the carbohydrate powder is selected from rice, corn, potatoes, wheat, barley, quinoa, sugar beats, sorghum, millet, oats, secale cereal, *Sorghum nigrum*, millet seeds, macadamia, walnuts, cashew nuts, black garlic, tomatoes, grape fruits, kumquat, apples, or any mixtures thereof at 10% to 18% by weight.

At step 204, a fiber powder having a fourth predetermined percentage (%) by weight is provided. In some implementations, the fiber powder is selected from carrots, red pumpkins, cashew nuts, walnuts, macadamia, *Matricaria chamomilla, Hypericum calycinum*, various vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, tumerics, or their combinations thereof at 1% to 5% by weight.

At step 205, the above ingredients in form of powder is and sieved or sintered all together to eliminate unwanted impurities. In one implementation of step 205, either stainless steel sieve pan or brass sieve pan having a fine opening size can be used.

At step 206, the food composition is micronized into a precisely tailored nano-scaled food composition. In many implementations of step 206 of the present invention, modern micronization techniques such as Rapid Expansion of Supercritical Solutions (RESS), Supercritical Anti-Solvent (SAS), or Particles from Gas Saturated Solutions (PGSS)

can be used to grind the food composition to 1-100 nm nanoscale dimension. These micronization techniques are well-known in the art for reducing food products into nanoscale foods and therefore they are not discussed in details therein. In other implementations of step 206, milling, bashing, and grinding techniques can also be used.

At step 207, purified water having a fifth predetermined percentage (%) by weight is added into the sieved food composition. In one exemplary implementation, the amount of purified water added into the food composition is 65% to 90% by weight.

At step 208, the purified water and powder food composition is mixed together and precooked until the food composition become a liquid phase. More particularly, the food composition is heated up to the temperature between 80 to 100° C. for 10 to 30 minutes to open up all the ingredients.

At step 209, an enzyme group having a fourth predetermined percentage (%) by weight is added into the liquid composition from step 208. In one implementation of step 209, enzyme group is selected from cellulase enzyme, amylase enzyme, lipase enzyme, and protease enzyme at 0.01% to 2% weight.

At step 210, the liquid food composition mixed with enzyme is undergone a hydrolysis process during which the pH level, viscosity, temperature is measured and checked periodically at 15 minute interval until the process is finished.

At step 211a, after the hydrolysis process ends, soybean oils, salt, and medium chained triglycerides (MCT) is are allowed to dissolve into the composition. The aim of step 211a is to increase the food value and improve the tastes and feels of the food composition.

At step 211b, after adding the above described ingredients, dissolvable fiber supplement powder is added to ensure the fiber content of the food products for the consumers.

Next, at step 212, the food composition is undergone a filtration and homogenization process. In one implementation, the food composition is homogenized to create a uniform product and then food composition is filtered by passing through to a Millipore membrane and an Amicon centrifugal filter unit, which guarantees the composition is in an uniform liquid form. Millipore membrane and Amicon centrifugal filter unit are well known in the art and need not to be discussed here.

At step 213, a supplement composed of minerals, vitamins, and amino acids having a sixth predetermined percentage (%) by weight is added to the food composition. In one implementation of the present invention, the minerals and vitamins are selected from a group of vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine at 0.01% to 3% weight.

At step 214, the food composition is sterilized to eliminate all form of bacterial. In some implementations of step 214, an ultra-heat treatment (UHT) process is used to sterilize the food composition at 135 to 142 degrees Celsius.

At step 215, same vitamins, minerals, and amino acids are added again in the food composition lest they are reduced during the sterilization process of step 214.

From here on, the food composition is either transformed into an instant food or a fresh food. From step 216 to 219, the food composition is turned into an instant food in a package. On the other hand, from steps 220 to 221, the food composition is maintained as a fresh food in a package. In some aspects of the present invention, instant food is, but is not limited to, dissolvable powders.

At step 216 safe food additives are added to the instant food formula. In some implementations of step 216 the following example of safe foods additives are used including but not limited to inulin, lecithin, cellulose, riboflavin, natamycin, and ascorbyl palmitate, and maltodextrin.

Now referring to step 217 the sterilized liquid food composition is dried to transform it into an instant food formula. In some implementations, step 217 is realized by a freeze drying process by a drying process including, but not limited to, freeze drying, cold drying, and hot drying, etc. In other implementations, super-speed centrifugal drying process is employed. Freeze drying process, cold drying, hot drying and super-speed centrifugal drying process are well-known in the art and they are not discussed in details.

At step 218, the instant food formula is packaged. The process of food packaging is well known in the art and therefore will not be discussed here.

At step 219, the final instant food formula of the present invention as described from steps 201-218 above is obtained having calorie density of 1 kcal/ml, a viscosity less than 100 cP, a peptide less than 10 kDa, and amino acids such as leucine, aspartic acid, alanine, tyrosine, threonine, valine, lysine, serine, isoleucine, histidine, glutamic acid, methionine, cysteine, proline, tryptophan, phenylalanine, glycine, and arginine is achieved. In some implementations, vitamin group such as vitamins are selected from a group of vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium (vitamin D), iron, zinc, phosphate, and iodine is also added into the instant food formula. The instant food formula in accordance with the present invention can be administered either by mouth or enteral feeding tube. The instant oral/enteral food formula of the present invention is a ready-to-eat food. In oral administration method, a user only needs to open the package, pour the food formula in form of dissolvable powders in a bowl and pour warm water therein, wait for 5-10 minutes, and the food in form of liquid are ready to serve. In enteral administration method, after the food formula is mixed with warm water for 5-10 minutes, the liquid food formula can be administered to the patient by a tube-feeding method.

At steps 220 and 221, the fresh food is packaged and the final oral/ethereal food of the present invention having a calorie density of 1 kcal/ml, a viscosity less than 100 cP, chain peptide less than 10 kDa, and a plurality of amino acids including a leucine, an aspartic acid, an alanine, a tyrosine, a threonine, a valine, a lysine, a serine, an isoleucine, a histidine, a glutamic acid, a methionine, a cysteine, a proline, a tryptophan, a phenylalanine, a glycine, and an arginine is achieved. In some other implementation, a vitamin group selected from a group of vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium (vitamin D), iron, zinc, phosphate, and iodine is also added into the fresh food package.

Figure 3:
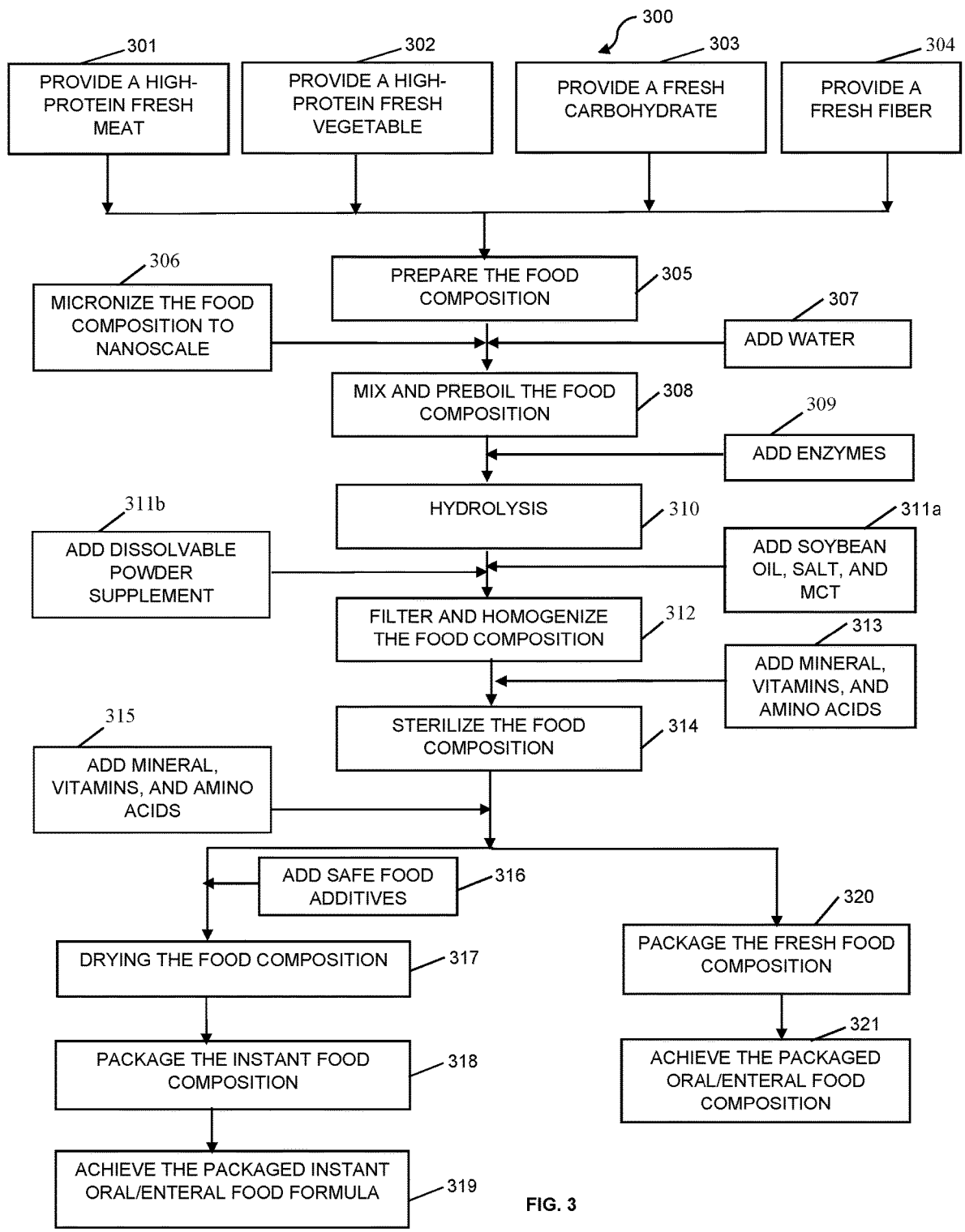
FIG. 3 is a flowchart illustrating a process of manufacturing an oral/enteral food of the present invention from fresh ingredients.

Next referring to FIG. 3, a process 300 of manufacturing oral/enteral foods in forms of instant food formula or fresh nutritious food composition from various fresh ingredients are illustrated. In some implementations, process 300 is used to produce either an instant oral or enteral food formula in a package. In some other implementations, process 300 is used to produce a nutritious oral or enteral food composition in a package. In this instant, the food composition is ready to be used by either oral or enteral administration method.

At step 301, a high-protein fresh meat group having a first predetermined percentage (%) by weight is prepared. In one implementation, the fresh meat group is selected generally from farm animals such as pork, beefs, goats, and lambs, etc. and other cattles; chickens, ducks, and other fowls such as turkeys; seafoods such as shrimps and all sorts of fishes; and edible insects such as crickets, larvae, grasshoppers, beetles, flies totaled to 8% to 15% by weight. In some implementations, the standards to select fresh pork meat is discussed in Table 3 above is used.

At step 302, a high-protein fresh vegetable group having a second predetermined percentage by weight is provided. In one exemplary implement of this step, the fresh vegetable food group is selected from a group of Vietnamese gingsen (*Panax vietnamensis*), *Angelica sinensis* gingsen, *Curculigo orchioides, Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, *Lentinula edodes*, oyster mushroom (*Pleurotus eryngii*), or combinations thereof totaled to 2% to 7% by weight. In some implementations, the standards to select fresh vegetable group discussed in Table 2 above is used.

At step 303, a fresh carbohydrate food group having a third predetermined percentage (%) by weight is provided. In one exemplary embodiment, the carbohydrate food group is selected from rice, corn, potatoes, wheat, barley, quinoa, sugar beets, sorghum, millet, oats, secale cereal, *Sorghum nigrum*, millet seeds, macadamia, walnuts, cashew nuts, black garlic, tomatoes, grape fruits, kumquat, apples, or any mixtures thereof at 10% to 18% by weight.

At step 304, a fresh fiber food group having a fourth predetermined percentage (%) by weight is provided. In some implementations, the fiber food group is selected from carrots, red pumpkins, cashew nuts, walnuts, macadamia, *Matricaria chamomilla, Hypericum calycinum*, different vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, tumerics, or their combinations thereof at 1% to 5% by weight of the food composition.

At step 305, the above fresh food groups are prepared. In one implementation of step 305, standards indicated Table 2 and Table 3 are used to prepare the fresh food groups.

At step 306, the food composition is micronized into a precisely tailored nano-scaled food composition. In many implementations of step 306 of the present invention, modern micronization techniques such as Rapid Expansion of Supercritical Solutions (RESS), Supercritical Anti-Solvent (SAS), or Particles from Gas Saturated Solutions (PGSS) can be used. These micronization techniques are well-known in the art for reducing food products into nanoscale foods and therefore they are not discussed in details therein. In other implementations of step 306, milling, bashing, and grinding techniques can also be used.

At step 307, purified water having a fifth predetermined percentage (%) by weight is added into the sieved food composition. In some implementations, the amount of purified water added is 50% to 80% by weight.

At step 308, the purified water and the fresh food composition is mixed together and precooked. The purified water and the fresh food composition are mixed together and well cooked between 10 to 30 minutes in a normal condition.

At step 309, an enzyme group having and said sixth predetermined percentage (%) by weight is added into the liquid composition from step 308. In one implementation of step 309, enzyme group is selected from cellulase enzyme, amylase enzyme, lipase enzyme, and protease enzyme at 0.01% to 3% weight. In some implementations, enzymes in accordance with Table 4 above are used.

At step 310, the food composition mixed with enzyme is undergone a hydrolysis process during which pH level, viscosity, temperature is periodically measured and checked at a 15 minute interval until the process is finished.

At step 311a, after the hydrolysis process ended, soybean oils, salt, and medium chained triglycerides (MCT) is are allowed to dissolve into the composition. The aim of step 311a is to increase the food value and improve the tastes and feels of the composition.

At step 311b, after adding the above described ingredients, dissolvable fiber powder is added to ensure the fiber content of the food products is met for the consumers.

Next, at step 312, the food composition is undergone a filtration and homogenization process. In one implementation, the food composition is homogenized to create a uniform product and then food composition is filtered by passing through to a Millipore membrane and an Amicon centrifugal filter unit, which guarantees the composition is in a uniform liquid form. Millipore membrane and Amicon centrifugal filter unit are well known in the art and need not to be discussed here.

At step 313, a supplement composed of minerals, vitamins, and amino acids having a seventh predetermined percentage (%) by weight is added to the food composition. In one implementation of the present invention, the minerals and vitamins are selected from a group of vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium (K), sodium (Na), magnesium (Mg), calcium (Ca), iron (Fe), zinc (Zn), phosphate (P), and iodine (I) at 0.01% to 3% weight.

At step 314, the food composition is sterilized to eliminate all form of bacteria. In some implementations of step 314, an ultra-heat treatment (UHT) process is used to sterilize the food composition to 135-142 degrees Celsius to produce a safe food product.

At step 315, same vitamins and minerals are added again in the food composition lest they are reduced during the sterilization process of step 314.

From here on, the food composition is either transformed into an instant food or a fresh food. From step 316 to 319, the food composition is turned into an instant food in a package. On the other hand, from steps 320 to 321, the food composition is maintained as a fresh food in a package.

At step 316, safe food additives are added to the instant food formula. In some implementations, the following example safe foods additives are used inulin, lecithin, cellulose, riboflavin, natamycin, and ascorbyl palmitate, maltodextrin.

Now referring to step 317, the sterilized liquid food composition is dried to transform it into an instant food formula. In some implementations, step 317 is realized by a freeze drying process, cold drying and hot drying processes, etc. In other implementations, super-speed centrifugal drying process is employed. Freeze drying process, cold drying process, hot drying process and super-speed centrifugal drying process are well-known in the art and they are not discussed in details.

At step 318, the instant food formula is packaged. The process of food packaging is well known in the art and therefore will not be discussed here.

Finally at step 319, the instant food formula is obtained having calorie density of 1 kcal/ml, a viscosity less than 100 cP, and chain peptides less than 10 kDa, plurality of amino acids including a leucine, an aspartic acid, an alanine, a tyrosine, a threonine, a valine, a lysine, a serine, an isoleucine, a histidine, a glutamic acid, a methionine, a cysteine, a proline, a tryptophan, a phenylalanine, a glycine, and an arginine, and a group of vitamins selected from vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine is achieved. The instant food formula in form of dissolvable powders in accordance with the present invention can be administered either by mouth or enteral. The instant oral/enteral food formula of the present invention is a ready-to-eat food.

At steps 320 and 321, the fresh food is packaged and the final oral/ethereal food of the present invention having a calorie density of 1 kcal/ml, a viscosity less than 100 cP, a peptide less than 10 kDa, and a plurality of amino acids including a leucine, an aspartic acid, an alanine, a tyrosine, a threonine, a valine, a lysine, a serine, an isoleucine, a histidine, a glutamic acid, a methionine, a cysteine, a proline, a tryptophan, a phenylalanine, a glycine, and an arginine; a group of vitamins selected from vitamin A, vitamin $D_3$, vitamin E, vitamin vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine is achieved.

Figure 4:
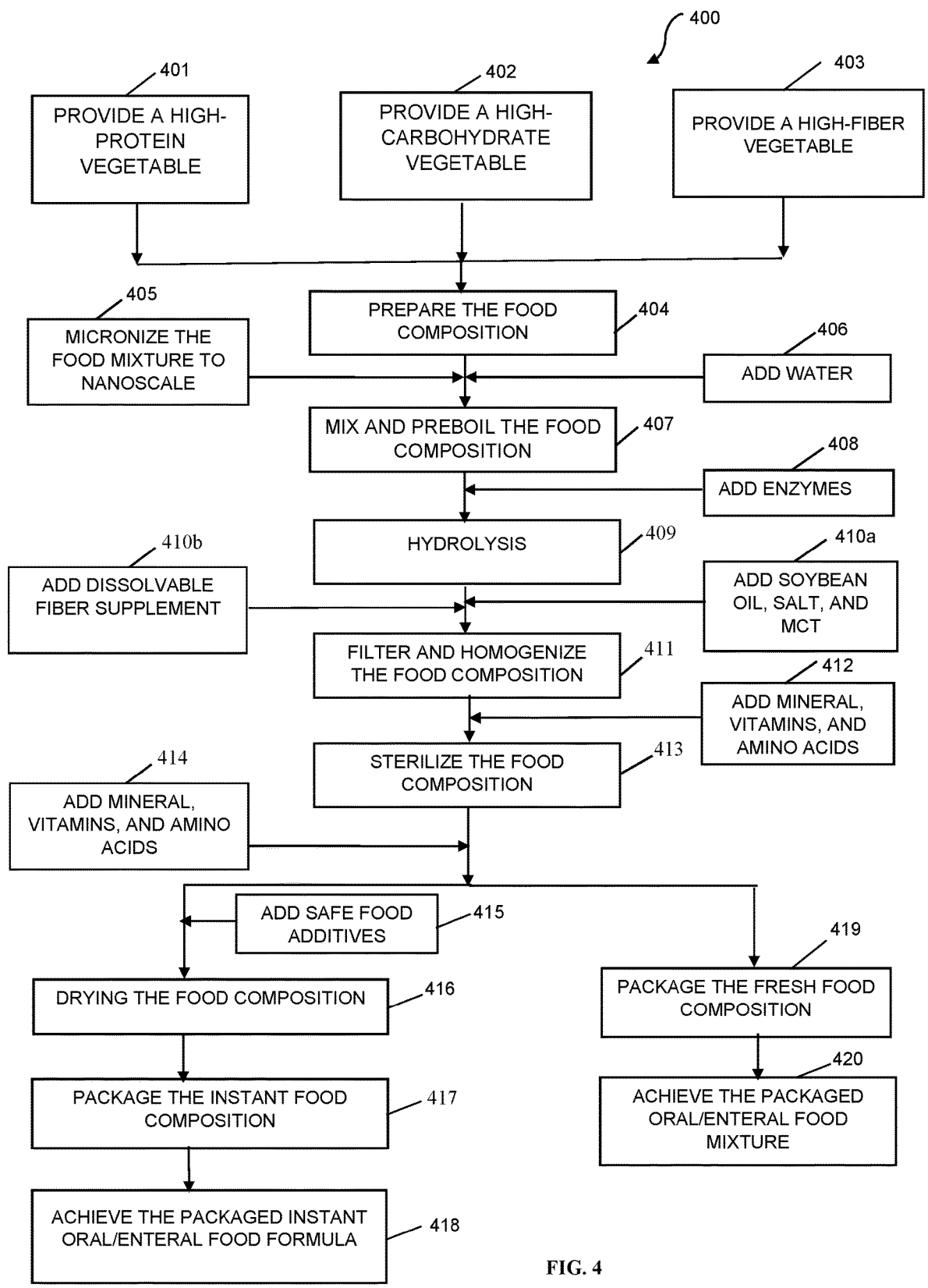
FIG. 4 is a flow chart illustrating a process of manufacturing an oral/enteral vegetarian food composition in accordance with an exemplary embodiment of the present invention.

Next referring to FIG. 4, a process 400 of manufacturing oral/enteral foods for vegetarians are illustrated. In some implementations, process 400 is used to produce either an instant oral or enteral food formula in a package. In some other implementations, process 400 is used to produce a nutritious oral or enteral food composition in a package. In this instant, the food is ready to be used by either oral or enteral administration method.

At step 401, a high-protein fresh vegetable group having a first predetermined percentage by weight is provided. In one exemplary implementation of this step, the fresh vegetable food group is selected from a group of Vietnamese gingsen (*Panax vietnamensis*), *Angelica sinensis* gingsen, *Curculigo orchioides, Panax pseudoginseng*, South Koreran gingsen, North Korean gingsen, Peruvian gingsen, *Ophiocordyceps sinensis* (cartepillar fungus), *Abelmoschus sagittifolius*, American gingsen (*Panax quinquefolius*), *Polyscias fruticosa*, Lotus rhizome, soy bean, *Glycine max*, green bean, potatoes, carrots, red pumpkins, macadamia, walnuts, almonds (amydala), *Momordica cochinchinensis*, green algae, curly kale, seaweeds, cauliflower, medicinal plants, medicinal herbs, chenopodium quinoa, avocado, spinach, cashew nuts, chia seeds, paddy straw mushrooms, *Lentinula edodes*, oyster mushroom (*Pleurotus eryngii*), or combinations thereof at 1% to 20% by weight. In some implementations, the standards to select fresh vegetable group discussed in Table 2 above is used.

At step 402, a fresh carbohydrate food group having a second predetermined percentage (%) by weight is provided. In one exemplary implementation, the carbohydrate food group is selected from rice, corn, potatoes, wheat, barley, quinoa, sugar beats, sorghum, millet, oats, secale cereal, *Sorghum nigrum*, millet seeds, macadamia, walnuts, cashew nuts, black garlic, tomatoes, grape fruits, kumquat, apples, or any mixtures thereof at 10% to 23% by weight.

At step 403, a fresh fiber food group having a third predetermined percentage (%) by weight is provided, in some implementations, the fiber food group is selected from carrots, red pumpkins, cashew nuts, walnuts, macadamia, *Matricaria chamomilla, Hypericum calycinum*, various vegetables, spinach, cauliflower, sweet potato, taro, different nuts such as black bean, red beans, peas, etc.; corn, artichokes flowers, chia seeds, lotus seeds, green tea, celery, catnip, *Morinda officinalis*, black garlic, cabbage, strawberries, pears, banana, blackberries, apple, avocado, kiwi fruits, passion fruit, lemon, cucumbers, cantaloupes, *Ginkgo biloba*, aloe vera, moringa, saffron, turmeric, or their combinations thereof at 1% to 10% by weight.

At step 404, the above fresh food groups are prepared. In one implementation of step 404, standards indicated Table 2 are used to prepare the fresh food groups.

At step 405, the food composition is micronized into a precisely tailored nano-scaled food composition. In many implementations of step 405 of the present invention, modern micronization techniques such as Rapid Expansion of Supercritical Solutions (RESS), Supercritical Anti-Solvent (SAS), or Particles from Gas Saturated Solutions (PGSS) can be used. These micronization techniques are well-known in the art for reducing food products into nanoscale foods and therefore they are not discussed in details therein. In other implementations of step 405, milling, bashing, and grinding techniques can also be used.

At step 406, purified water having a sixth predetermined percentage (%) by weight is added into the sieved food composition. In some embodiment, the amount of purified water is 40% to 85% by weight.

At step 407, the water and the fresh food composition is mixed together and well cooked between 10 to 30 minutes in the normal conditions.

At step 408, an enzyme group having and said fourth predetermined percentage (%) by weight is added into the liquid composition from step 407. In one implementation of step 408, enzyme group is selected from cellulase enzyme, amylase enzyme, lipase enzyme, and protease enzyme at 0.01% to 5% weight. In some implementations, enzymes in accordance with Table 4 above are used.

At step 409, the food composition mixed with enzyme is undergone a hydrolysis process during which pH level, viscosity, and temperature are periodically measured and checked at a 15 minute time interval until this process is complete.

At step 410a, after the hydrolysis process ended, soybean oils, salt, and medium chained triglycerides (MCT) is are allowed to dissolve into the composition. The aim of step 410a is to increase the food value and improve the tastes and feels of the composition.

At step 410b, after adding the above described ingredients, dissolvable fiber is added to ensure the fiber content of the food products for the consumers.

Next, at step 411, the food composition is undergone a filtration and homogenization process. In one implementation, the food composition is homogenized to create a uniform product and then food composition is filtered by passing through to a Millipore membrane and an Amicon centrifugal filter unit, which guarantees the composition is in a uniform liquid form. Millipore membrane and Amicon centrifugal filter unit are well known in the art and need not to be discussed here.

At step 412, a supplement composed of minerals, vitamins, and amino acids having a fifth predetermined percentage (%) by weight is added to the food composition. In one implementation of the present invention, the minerals and vitamins are selected from a group of vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine at 0.01% to 3% by weight.

At step 413, the food composition is sterilized to eliminate all form of bacteria. In some implementations of step 413, an ultra-heat treatment (UHT) process is used to sterilize the food composition to 135-142 degrees Celsius.

At step 414, same vitamins and minerals are added again in the food composition lest they are reduced during the sterilization process of step 413.

From here on, the food composition is either transformed into an instant food or a fresh food. From step 415 to 418, the food composition is turned into an instant food in a package. On the other hand, from steps 419 to 420, the food composition is maintained as a fresh food in a package.

At step 415, safe food additives are added to the instant food formula. In some implementations, the following example safe foods additives are used inulin, lecithin, cellulose, riboflavin, natamycin, ascorbyl palmitate, and maltodextrin.

Now referring to step 416, the sterilized liquid food composition is dried to transform it into an instant food formula. In some implementations, step 416 is realized by a free drying process, hot drying process, or a cold drying process, etc. In other implementations, super-speed centrifugal drying process is employed. Free drying process, cold drying process, hot drying process, and super-speed centrifugal drying process are well-known in the art and they are not discussed in details.

At step 417, the instant food formula for vegetarians is packaged. The process of food packaging is well known in the art and therefore will not be discussed here.

At step 418, the instant food formula for vegetarians is obtained having calorie density of 1 kcal/ml, a viscosity less than 100 cP, and peptide less than 10 kDa, plurality of amino acids including a leucine, an aspartic acid, an alanine, a tyrosine, a threonine, a valine, a lysine, a serine, an isoleucine, a histidine, a glutamic acid, a methionine, a cysteine, a proline, a tryptophan, a phenylalanine, a glycine, and an arginine is achieved. In some other implementations, vitamins including vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine is also added into the instant food formula. The instant food formula in form of dissolvable powders in accordance with the present invention can be administered either by mouth or enteral. The instant oral/enteral food formula of the present invention is a ready-to-eat food.

At steps 419 and 420 the fresh food for vegetarians is packaged and the final oral/ethereal food of the present invention having a calorie density of 1 kcal/ml, a viscosity less than 100 cP, a peptide less than 10 kDa, and a plurality of amino acids including a leucine, an aspartic acid, an alanine, a tyrosine, a threonine, a valine, a lysine, a serine, an isoleucine, a histidine, a glutamic acid, a methionine, a cysteine, a proline, a tryptophan, a phenylalanine, a glycine, and an arginine is achieved. In other implementation, vitamins including vitamin A, vitamin $D_3$, vitamin E, vitamin $B_1$, vitamin $B_2$, vitamin $B_3$, vitamin $B_6$, vitamin $B_{12}$, vitamin $B_5$, vitamin C, biotin, folic acid, potassium, sodium, magnesium, calcium, iron, zinc, phosphate, and iodine is also added into the final oral/ethereal food.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A process of manufacturing an oral and enteral tube-feeding vegetarian food composition in a package, comprising:
   (a) preparing a vegetarian food composition by selecting and combining high-protein vegetable food ingredients having a first predetermined percentage (%) by weight, carbohydrate ingredients having a second predetermined percentage (%) by weight, and fiber ingredients having a third predetermined percentage (%) by weight according to a predetermined quality guideline;
   (b) sieving said vegetarian food composition;
   (c) precooking and pulverizing said food composition;
   (d) adding purified water having a sixth predetermined percentage (%) by weight;
   (e) enzymatically hydrolyzing said food composition by first adding enzymes comprising a cellulase enzyme, an amylase enzyme, and a protease enzyme to said food composition obtained in step (d), and then by incubating said food composition with said enzymes, said enzymes having a fourth predetermined percentage (%) of weight;
   (f) adding a supplement of minerals and vitamins having a fifth percentage (%) by weight into said food composition after said enzymatic hydrolyzing step;
   (g) filtering and homogenizing said food composition of said step (f);
   (h) sterilizing said food composition of said step (g);
   (i) drying said food composition of said step (i); and
   (j) packaging said food composition of said step (i).

2. The process of claim 1 wherein said first predetermined percentage (%) by weight is 1% to 20%, said second predetermined percentage (%) by weight is 10% to 23%, said third predetermined percentage (%) by weight is between 1% to 10%, said fourth predetermined percentage (%) by weight is 0.01% to 5%, said fifth predetermined percentage (%) by weight is between 0.01% to 3%, and said sixth predetermined percentage (%) by weight is between 40% to 85% of the total weight of said food composition; and, after step (e) adding and mixing soybean oil, salt, and medium chain triglycerides (MCT) to said food composition after said enzymatic hydrolyzing step until said tube-feeding food composition has a calorie density of 1 kcal/ml; peptides less than 10 kDa in molecular weight; a viscosity less than 100 cP; and a plurality of amino acids including leucine, aspartic acid, alanine, tyrosine, threonine, valine, lysine, serine, isoleucine, histidine, glutamic acid, methionine, cysteine, proline, tryptophan, phenylalanine, glycine, and arginine.

3. The process of claim 1 wherein said minerals and vitamins comprise vitamin A, vitamin $D_3$, vitamin E, vitamin $B_1$, vitamin $B_2$, vitamin $B_3$, vitamin $B_6$, vitamin $B_{12}$, vitamin B$_5$, vitamin C, biotin, folic acid, potassium, sodium, magnesium, calcium, iron, zinc, phosphate, and iodine.

4. The process of claim 1 wherein said high protein vegetable ingredients comprise: Vietnamese gingseng (*Panax vietnamensis*), *Angelica sinensis* gingseng, *Curculigo orchioides, Panax pseudoginseng*, South Korean gingseng, North Korean gingseng, Peruvian gingseng, *Ophiocordyceps sinensis* (catepillar fungus), *Abelmoschus sagittifolius*, American gingseng (*Panax quinquefolius*), *Polyscias fruticosa*, lotus rhizome, soy bean, *Glycine max*, green bean, potatoes, carrots, red pumpkins, macadamia nuts, walnuts, almonds, *Momordica cochinchinensis*, green algae, curly kale, seaweeds, cauliflower, chenopodium quinoa, avocado, spinach, cashew nuts, chia seeds, Daddy straw mushrooms, *Lentinula edodes*, oyster mushroom (*Pleurotus eryngii*), and fungi.

5. The process of claim 4 wherein said carbohydrate ingredients comprise rice, corn, potatoes, wheat, barley, quinoa, sugar beets, sorghum, millet, oats *Secale cereale* (rye), *Sorghum nigrum*, millet seeds, macadamia nuts, walnuts, cashew nuts, black garlic, tomatoes, grapefruits, kumquat, and apples.

6. The process of claim 4 wherein said fiber ingredients comprise carrots, red pumpkins, cashew nuts, walnuts, macadamia nuts, *Matricaria chamomilla, Hypericum calycinum*, spinach, cauliflower, sweet potato, taro, nuts, corns, artichokes, chia seeds, lotus seeds, green tea, celery, catnip, *Morinda officinalis*, black garlic, cabbage, strawberries, pears, banana, blackberries, apples, avocados, kiwi fruit, passion fruit, lemon, cucumber, cantaloupe, *Ginkgo biloba*, aloe vera, moringa, saffron, and turmeric.

7. The process of claim 4 wherein said high protein vegetable ingredients further comprise red beans, green beans, and peas.

8. The process of claim 4 wherein said fungi comprise *Lentinula edodes, Volvariella volvacea*, and *Pleurotus eryngii*.

9. The process of claim 1 wherein said dried food composition of step (i) is a dissolvable powder.

10. The process of claim 1, wherein said predetermined quality guideline comprises selecting said high-protein vegetable ingredients having a first predetermined percentage (%) by weight by weight by physical examination for cleanliness, aroma, freshness, shape, and viscosity, by fat content, by percentage of humidity, by protein content, and by percentage of impurities.

11. The process of claim 10, wherein said percentage of humidity is between 72.5 percent and 75.5 percent; and wherein said percentage of fat is between 1.2 percent ad 3 percent.

12. A vegetarian food composition, comprising:
a high-protein vegetable group having a first predetermined percentage (%) by weight; a carbohydrate group having a second predetermined percentage (%) by weight; and a fiber group having a third predetermined percentage (%) by weight; purified water having a sixth predetermined fourth percentage (%) by weight; an enzyme group having a fourth percentage (%) by weight; and a mineral and vitamin group having a fifth percentage (%) by weight, wherein said food composition is produced by a process comprising the following steps:
(a) preparing a food mixture by selecting and combining said high-protein vegetable group having said first predetermined percentage (%) by weight, said carbohydrate group having said second predetermined percentage (%) by weight, and said fiber group having said third predetermined percentage (%) by weight in accordance with a predetermined quality guideline;
(b) sieving said food composition;
(c) precooking and pulverizing said food composition;
(d) adding purified water having said sixth predetermined percentage (%) by weight;
(e) enzymatically hydrolyzing said food composition by adding enzymes having said fifth predetermined percentage (%) of weight;
(f) adding a supplement of a group of minerals and vitamins having said fifth percentage (%) by weight into said food composition after said enzymatic hydrolysis step;
(g) filtering and homogenizing said food composition;
(h) sterilizing said food composition;
(i) drying said food composition; and
(j) packaging said food composition.

13. The food composition of claim 12 wherein said first predetermined percentage (%) by weight is 1% to 20%, said second predetermined percentage (%) by weight is 10% to 23%, said third predetermined percentage (%) by weight is between 1% to 10%, said fourth predetermined percentage (%) by weight is 0.01%-5%, said fifth predetermined percentage (%) by weight is between 0.01 to 3%, and said sixth predetermined percentage (%) by weight is between 40% to 85% of the total weight of said food composition; and wherein said food composition further comprises soybean oil, salt, and medium chain triglycerides (MCT) that are combined and added to said food composition after step (e); and wherein step (e) is performed until said food composition has a calorie density of 1 kcal/ml; peptides less than 10 kDa in molecular weight; a viscosity less than 100 cP; and a plurality of amino acids including leucine, aspartic acid, alanine, tyrosine, threonine, valine, lysine, serine, isoleucine, histidine, glutamic acid, methionine, cysteine, proline, tryptophan, phenylalanine, glycine, and arginine.

14. The food composition of claim 12 wherein said mineral and vitamin group comprises vitamin A, vitamin D$_3$, vitamin E, vitamin B$_1$, vitamin B$_2$, vitamin B$_3$, vitamin B$_6$, vitamin B$_{12}$, vitamin B$_5$, vitamin C, biotin, folic acid, potassium, sodium, magnesium, calcium, iron, zinc, phosphate, and iodine.

15. The food composition of claim 12 wherein said high-protein vegetable group comprises Vietnamese gingseng (*Panax vietnamensis*), *Angelica sinensis* gingseng, *Curculigo orchioides, Panax pseudoginseng*, South Korean gingseng, North Korean gingseng, Peruvian gingseng, *Ophiocordyceps sinensis* (catepillar fungus), *Abelmoschus sagittifolius*, American gingseng (*Panax quinquefolius*), *Polyscias fruticosa*, lotus rhizome, soy bean, *Glycine max*, green bean, potatoes, carrots, red pumpkins, macadamia nuts, walnuts, almonds, *Momordica cochinchinensis*, green algae, curly kale, seaweeds, cauliflower, chenopodium quinoa, avocado, spinach, cashew nuts, chia seeds, paddy straw mushrooms, *Lentinula edodes*, oyster mushroom (*Pleurotus eryngii*), and fungi.

16. The food composition of claim 11 wherein said carbohydrate group comprises rice, corn, potatoes, wheat, barley, quinoa, sugar beets, sorghum, millet, oats, *Secale cereale* (rye), *Sorghum nigrum*, millet seeds, macadamia nuts, walnuts, cashew nuts, black garlic, tomatoes, grapefruits, kumquat, and apples.

17. The food composition of claim 16 wherein said enzymes having said fifth percentage by weight comprise a cellulase enzyme, an amylase enzyme, a lipase enzyme, and a protease enzyme.

18. The food composition of claim 15 wherein said fungi comprise *Lentinula edodes, Volvariella volvacea*, and *Pleurotus eryngii*.

19. The process of claim 12, wherein said predetermined quality guideline comprises selecting said high-protein vegetable group having a first predetermined percentage (%) by weight by physical examination for cleanliness, aroma, freshness, shape, and viscosity, by fat content, by percentage of humidity, by protein content, and by percentage of impurities.

20. The process of claim 18, wherein said preset percentage of humidity is between 72.5 percent and 75.5 percent; and wherein said preset percentage of fat is between 1.2 percent and 3 percent.

\* \* \* \* \*